United States Patent [19]

Kirsch

[11] Plant 4,887

[45] Sep. 14, 1982

[54] LILY NAMED MERCI

[75] Inventor: Ted T. Kirsch, Myrtle Point, Oreg.

[73] Assignee: Sun Valley Bulb Farms, Inc., Myrtle Point, Oreg.

[21] Appl. No.: 216,066

[22] Filed: Dec. 12, 1980

[51] Int. Cl.[3] ..... A01H 5/00
[52] U.S. Cl. ..... Plt./68
[58] Field of Search ..... Plt./68

*Primary Examiner*—Robert E. Bagwill

*Attorney, Agent, or Firm*—Chas. W. Rummler

[57] ABSTRACT

A new and distinct variety of Oriental Hybrid lily plant of the Parkmannis type, particularly distinguished by its flat, acutely-upright, reddish-pink flowers which have white undulating margins and which are borne in raceme arrangement on long, strong stems and strong, upright pedicels, usually with one bud or flower on each pedicel, and by its dark green, glossy and relatively disease-resistant foliage.

2 Drawing Figures

BACKGROUND OF THE NEW PLANT

My new variety of lily plant originated as a seedling of unknown parentage growing at my nursery in Arcata, Calif. Its brilliantly-colored, upwardly-facing flowers, vertically-disposed buds, and dark green, glossy foliage prompted me to asexually propagate this new variety for study at Arcata, Calif., during the course of which I found distinct and advantageous characteristics in the new plant which make it a valuable addition to the field of commercial lily culture for cut flower production. Propagation of this new lily plant through successive generations by means of scales and tissue culture at Arcata, Calif., has shown that its distinctive characteristics hold true from generation to generation and appear to be firmly fixed.

DESCRIPTION OF THE DRAWING

This new variety of lily plant is illustrated by the accompanying full color photographic drawing which shows a full grown blooming plant in the upper view and a close-up face view of a fully opened bloom in the lower view, the color rendition being as nearly true as can be obtained by conventional photographic procedures.

DESCRIPTION OF THE NEW PLANT

The following is a detailed description of my new variety of lily as observed at Arcata, Calif., with color designations according to the R.H.S. Colour Chart published by The Royal Horticultural Society of London, England, the observations having been made of greenhouse grown plants at Arcata, Calif., in the spring of 1980.

THE PLANT

Origin: Seedling.
Parentage: Unknown.
Classification: Oriental Hybrid, Parkmannis type.
Form: Tall single stem from each normal bulb, but two stems from large and older double-nose bulbs.
Height: About three feet at maturity.
Growth: Sturdy and upright, with excellent strength.
Cane size: Stems grow from about ¼ inch base diameter when the plant is at a height of about 1½ feet to about ¾ inch base diameter when the plant is at a height of 3 feet.
Foliage:
*Quantity.*—Abundant.
*Leaves at flower cluster.*—Three in number, varying from one at the base of each pedicel about 4½ inches long and 1 inch wide, to one on the pedicel approximately 1 inch from the flower bud and about 4 inches long and ¾ inch wide.
*Shape.*—Lanceolate.
*Texture.*—Leathery.
*Aspect.*—Smooth.
*Ribs and veins.*—Distinct longitudinal veins from base to tip.
Stem bulblets (underground):
*Occurrence.*—One to three on each healthy, normal plant at digging time.
*Size.*—From ¼ inch to 1 inch in diameter.
*Color.*—White, with occasional shading at the tips.
Bulbs:
*Size.*—From about 6 to 10 inches in circumference, depending upon age.
*Color.*—White, with yellow and pink overtones. As the bulbs become larger and older, the overtones of yellow and pink become more and more prominent.

THE BUD

Form: Lanceolate, with acuminate apex.
Size: Averaging about 3½ to 4 inches long and 1¾ inches in diameter.
Number: Usually one on each pedicel and with one to six buds on a plant stem according to culture and bulb size.
Opening rate: Normal; buds open successively from the lowermost bud to the top bud, which is the last to open.
Color: Whitish-pink at the tip of the bud, becoming a darker pink at the base when the sepals are about to divide and petals begin to unfurl.
Surface texture: Rugose and leathery, with prominent veins.
Pedicel: Strong and very upright; angled about 15° from the vertical.
*Color.*—Light green on under side and dark green on top side.
*Aspect.*—Glabrous.

*Length.*—About $3\frac{1}{2}$ to $4\frac{1}{2}$ inches.

THE FLOWER

Blooming habit: Annually, blooming profusely in July.

Size of flower: Medium, averaging about 6 to 7 inches in diameter.

Borne: From larger bulbs, the inflorescence has a raceme arrangement with each pedicel bearing one bud. The size of the bulb and its cultural care will determine the number of blooms and buds to be found on any given inflorescence. From large bulbs, this lily may have three to five blooms open at one time.

Shape: Generally flat, with uniformly-spaced petals in star arrangement, generally with the very tips of the petals curving backwardly and with the outer ends of the sepals curling backwardly and under.

Petalage: Normal; three sepals and three petals.

*Form.*—Sepals — Lanceolate with acuminate apex. Petals — Generally ovate with cuspidate apex and a center furrow bisecting each petal longitudinally. Edges of petals and sepals are sinuate; and the petals are about $4\frac{1}{2}$ inches long and about 2 inches wide at the widest part.

*Color.*—Upper side: Upon opening, the center of the petal is Red, RHS 46A, fading toward the margins to Greyed Purple, RHS 186D, and the inside half of the petals on either side of the center of the petal is moderately spotted with Dark Maroon oblong spots. There are no spots on the outer edges or tip of the petal. Under side: Red Purple, RHS 68D, and somewhat glabrous.

*Papillae.*—Present on the petals and from 4 to 8 in number.

*Texture.*—Leathery.

*Aspect.*—Velvety.

Fragrance: Sweet.

Discoloration: Color darkens somewhat as the bloom matures.

Effect of weather: Generally this flower is not affected by wet weather but ages somewhat as temperature rises.

Persistence: The flower tends to hang on and dry.

Lasting quality:

*On the plant.*—Two to three weeks depending on the size of the bulb and environmental temperature.

*As a cut flower.*—Ten days to two weeks.

REPRODUCTIVE ORGANS

Stamens:

*Anthers.*—Six in number, about 1 inch long, and in orderly arrangement around the pistil.

*Filaments.*—Length, about $2\frac{1}{2}$ inches. Color: Greenish-yellow.

Pistils:

*Number.*—One.

*Style.*—Length, about 3 inches. Color: Light green at the base, darkening somewhat at the stigma.

*Stigma.*—Color: Purple grey.

*Ovary.*—Classified as a schizocarp, about $2\frac{1}{2}$ to 3 inches long and $1\frac{1}{2}$ inches in diameter, dehiscing into thirds and containing six rows of seeds of the usual shape for lilies.

I claim:

1. A new and distinct variety of Oriental Hybrid lily plant, substantially as herein shown and described, characterized by its medium-large, upwardly-facing flowers borne on strong, stiff and close to vertically upstanding pedicels, and by its generally flat, moderately spotted and reddish-pink appearing petals on which the color fades laterally from a dark red central and longitudinally-extending stripe.

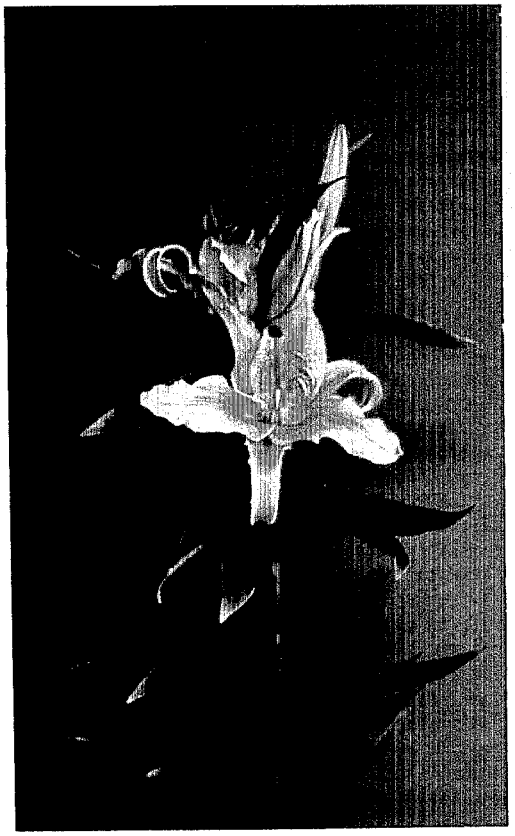
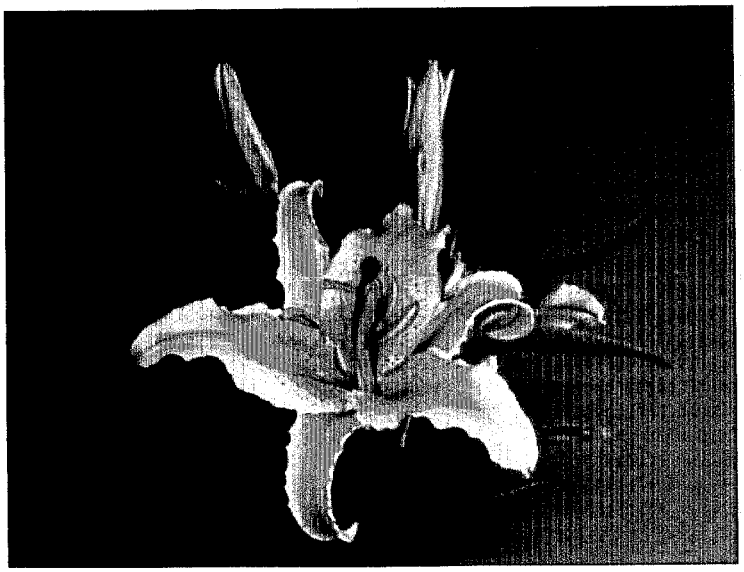

* * * * *